US008617111B2

(12) United States Patent
Stevenson (10) Patent No.: US 8,617,111 B2
(45) Date of Patent: Dec. 31, 2013

(54) ROTATIONAL ORIENTATION INDICATING HOLLOW NEEDLE ASSEMBLY (76) Inventor: Jon R. Stevenson, Powell, OH (US)

(*) Notice: Subject to any disclaimer, the term of this patent is extended or adjusted under 35 U.S.C. 154(b) by 0 days.

(21) Appl. No.: 13/343,284

(22) Filed: Jan. 4, 2012

(65) Prior Publication Data
US 2012/0172805 A1 Jul. 5, 2012

Related U.S. Application Data (60) Provisional application No. 61/429,528, filed on Jan. 4, 2011.

(51) Int. Cl.
*A61M 5/178* (2006.01)
(52) U.S. Cl.
USPC .................................. 604/164.01; 604/165.01
(58) Field of Classification Search
USPC ........................................ 604/164.01, 165.01
See application file for complete search history.

(56) References Cited

U.S. PATENT DOCUMENTS

2003/0171718 A1* 9/2003 DeLegge et al. ......... 604/164.01
2008/0294111 A1* 11/2008 Tal et al. .................. 604/165.01

FOREIGN PATENT DOCUMENTS

WO   WO2011109390 A2 * 9/2011

* cited by examiner

*Primary Examiner* — Nicholas Lucchesi
*Assistant Examiner* — Niyati D Shah
(74) *Attorney, Agent, or Firm* — Michael J. Gallagher; David J. Dawsey; Gallagher & Dawsey Co., LPA (57) ABSTRACT

A rotational orientation indicating hollow needle assembly having a needle, stylet, and hub. A hub sidewall has at least one external surface with at least one humanly tactilely discernible surface feature indicating the rotational relationship between the hub and the needle. Any portion of any of the assembly may bear indicia, or may be color-coded, to represent the size (gauge) of the needle, or needle type as an additional guide. In an exemplary embodiment the hub may be configured with two bevel face orientation features and two bevel orthogonal orientation features alternately spaced in a radial manner about the hub. An operator pinching the hub between a thumb and forefinger thus immediately feels these orientation features. When the assembly is rotated between the thumb and forefinger, these differing orientation features rotate as well, and the difference in tactile sensation immediately alerts the operator to the position of the needle bevel.

19 Claims, 15 Drawing Sheets

ROTATIONAL ORIENTATION INDICATING HOLLOW NEEDLE ASSEMBLY

CROSS-REFERENCE TO RELATED APPLICATIONS

This application claims the benefit of U.S. provisional patent application Ser. No. 61/429,528; filed on Jan. 4, 2011, all of which is incorporated by reference as if completely written herein.

TECHNICAL FIELD

The present invention relates generally to the field of hollow procedural needles, and in particular to a hollow procedural needle having an orientable exit port, the directionality of which may be ascertained from external indicia after a tip of the needle has been placed in tissue or otherwise obscured from view.

BACKGROUND OF THE INVENTION

In general, procedural needles are hollow needles typically used for a wide variety of medical procedures, and in some, but not all applications, are often traditionally referred to as "hypodermic" or "spinal" needles. Traditional procedural needles share a common trait. They generally have an exit port at or near the injection end of the needle, and this port may be at the needle end, or side, or most commonly, is central to a needle bevel, which provides a sharp point and makes the needle easier to push through skin or other tissues.

In needles having an exit port on the side, or as part of a bevel, therefore, there is a rotational orientation to the needle. The exit port, and/or bevel, may be directed in any direction around a 360 degree arc—and once the tip of the needle is inserted below the skin, it become very difficult to determine in which direction the exit port and/or bevel is pointing. There may be an index tab in the hub of the needle, often engaging a tab on the needle stylet, but this slot and tab arrangement is very small, and very difficult to feel.

Most typically, needles are inserted by having the operator grasp the needle hub in a pinching action between the thumb and forefinger, and what has long been needed is a needle assembly in which a humanly tactile discernible feature or features on the needle assembly itself gives the operator the information, continuously and without needing to visually check, the position of a hidden bevel of a partially inserted needle.

BRIEF DESCRIPTION OF THE DRAWINGS

Without limiting the scope of the present invention as claimed below and referring now to the drawings and figures:

These drawings are provided to assist in the understanding of the exemplary embodiments of the invention as described in more detail below and should not be construed as unduly limiting the invention. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

The present invention includes a rotational orientation indicating hollow needle assembly. The invention enables a significant advance in the state of the art. The preferred embodiments of the apparatus accomplish this by new and novel methods that are configured in unique and novel ways and which demonstrate previously unavailable but preferred and desirable capabilities. The description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

As seen in FIGS. 1-15, the system of the present invention provides a rotational orientation indicating hollow needle assembly (10) formed generally of three sub-assemblies. The first sub-assembly is a needle (100) having a needle lumen (110) surrounded at least in part by a needle sidewall (115), as seen well in FIGS. 9 and 12. The assembly (10) has a needle proximal end (105) and a needle distal end (155), seen well in FIG. 2. Throughout this specification, the term "proximal" shall mean that portion of the assembly (10) closest to the patient or subject when the assembly (10) is in use, and the term "distal" shall mean that portion of the assembly that is most distant from the patient or subject when the assembly (10) is in use. The assembly has a needle port (120) that places the needle lumen (110) in fluid communication with an external atmosphere, seen well in FIG. 9. Additionally, throughout this specification, the term "bevel" shall also include the side-port hollow needles having needle ports on the needle sidewall (115), such as the "Tuohy" style epidural needle, or various other side-port needle designs. In such cases, the directionality of the term "bevel" shall be equated to the directionality of the side-port needle port (125). The "lumen side" shall refer to the exit port side of any beveled or side port needle.

Figure 3:
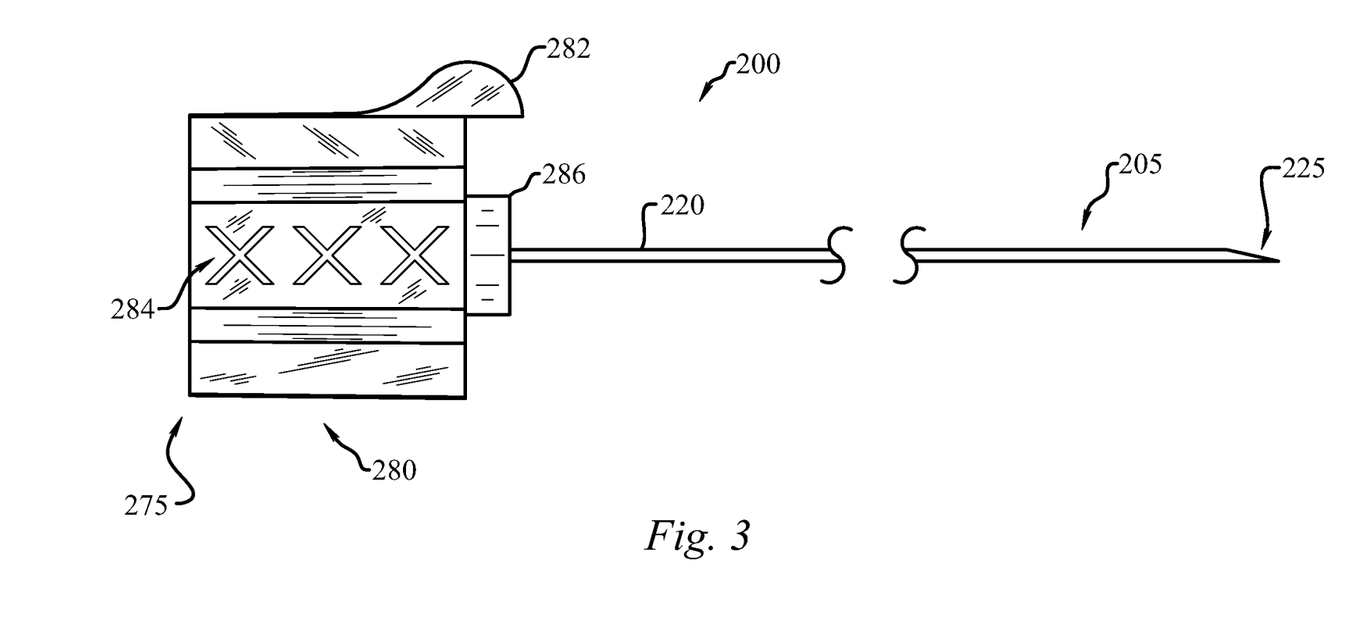
FIG. 3 is a side view of a portion of the embodiment of FIG. 1.

The assembly has a stylet (200), seen well in FIG. 3, substantially reversibly occluding the needle lumen (110) when in an insertion position into a patient or subject. Again with reference to FIG. 3, the stylet (200) includes a stylet shaft (220) with a stylet proximal end (205) and a stylet distal end (275), and a stylet base (280).

Figure 4:
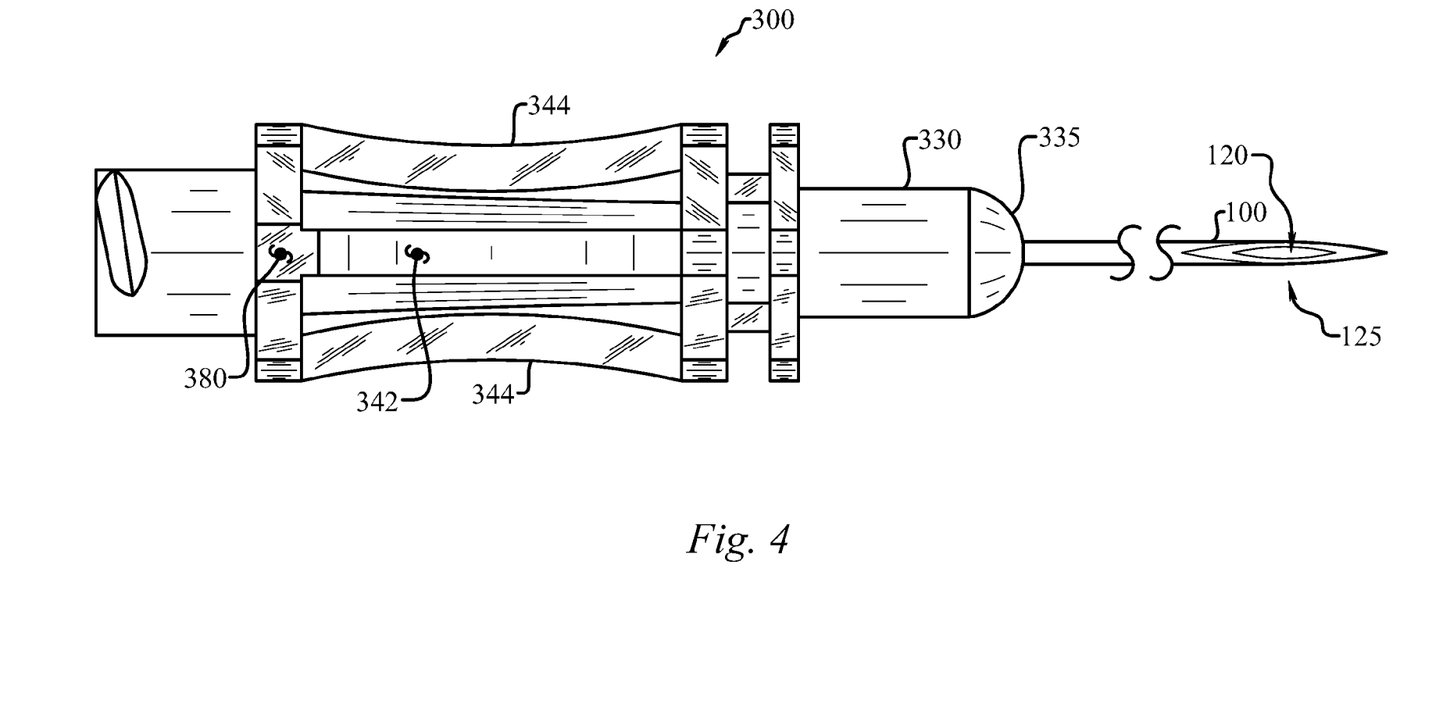
FIG. 4 is a top view of a portion of the embodiment of FIG. 1.
Figure 6:
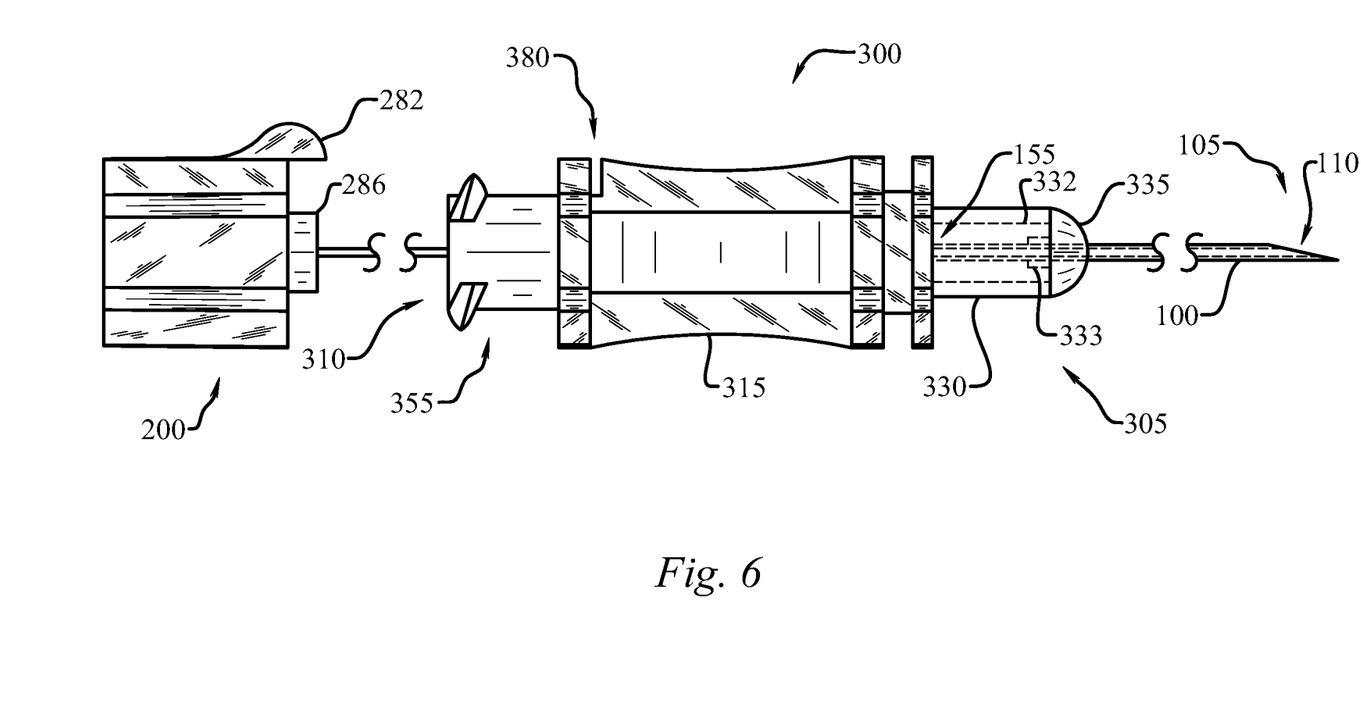
FIG. 6 is a partially exploded side view of a portion of the embodiment of FIG. 1.
Figure 10:
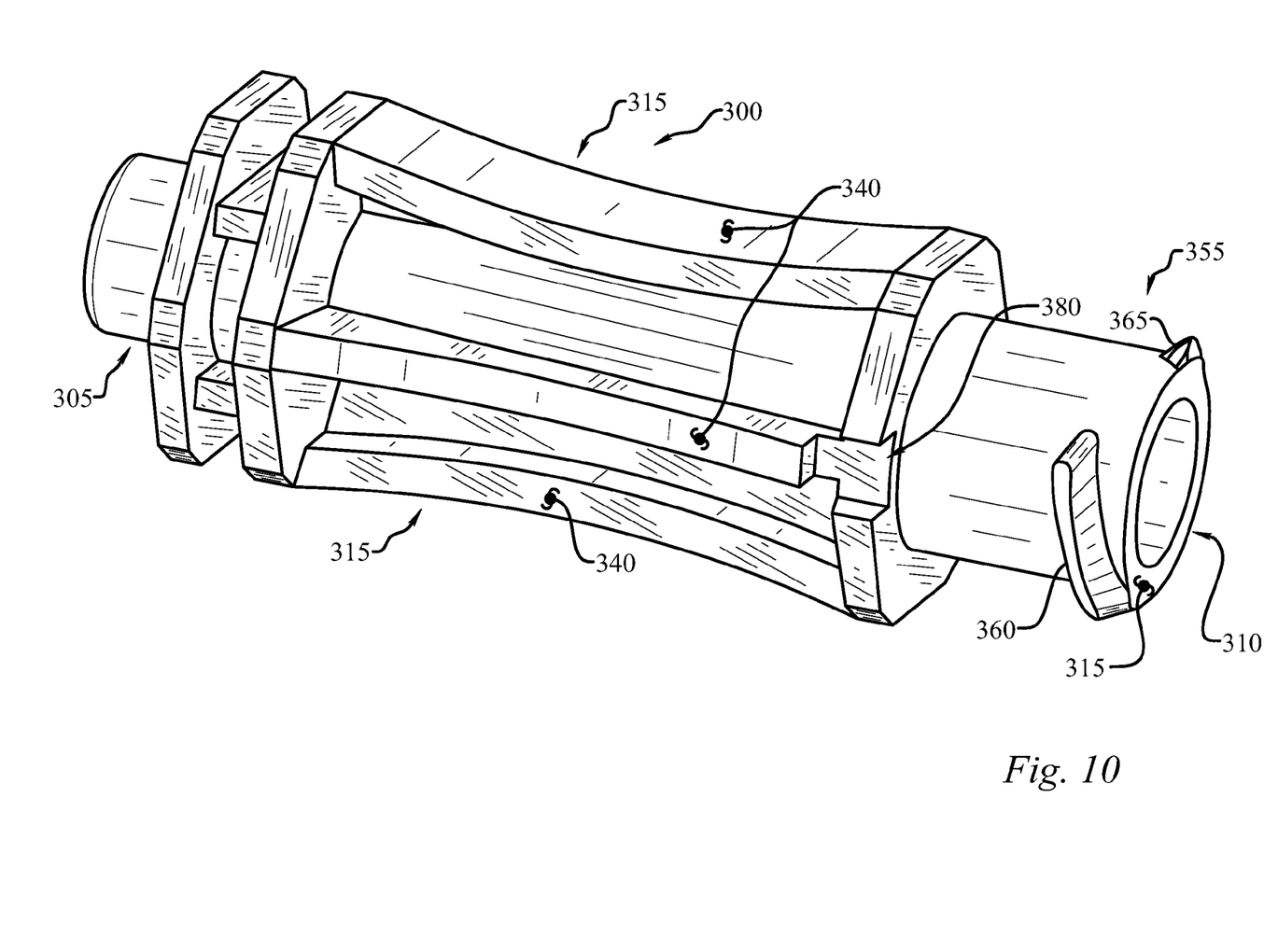
FIG. 10 is an elevated perspective view of a portion of the embodiment of FIG. 1.
Figure 11A:
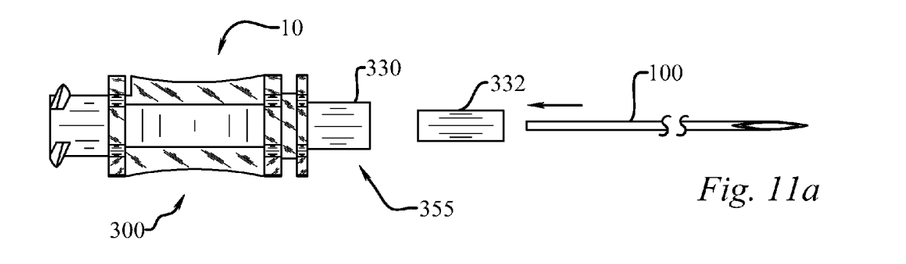
FIGS. 11*a*-11*c* are a series of partially exploded views showing partial assembly methods of an embodiment of FIG. 1.
Figure 11B:
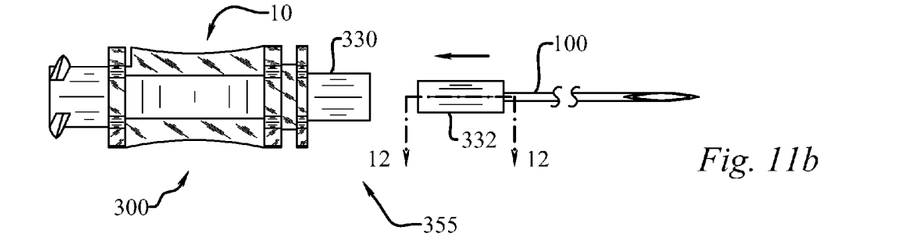
Figure 11C:
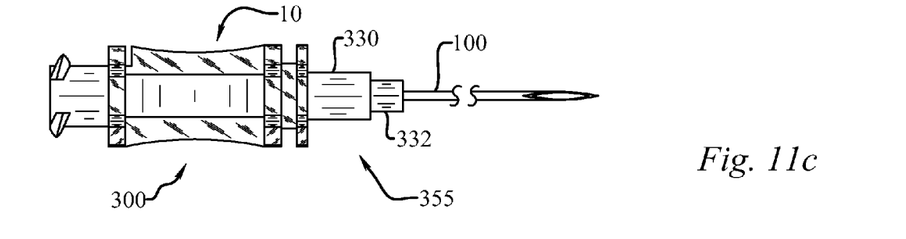

The assembly (10), at its distal end, has a hub (300), seen well in FIGS. 4 and 6, having a hub lumen (310) surrounded at least in part by a hub sidewall (315), connecting a hub proximal end (305) and a hub distal end (355), seen well in FIGS. 6 and 10. The hub proximal end (305) is attached in a predetermined rotational relationship to the needle distal end (155) at a hub-needle attachment (330), seen well in FIG. 8. This places the hub lumen (310) in fluid communication with the needle lumen (110). As seen well in FIG. 10, the hub sidewall (315) has at least one external surface formed with at least one humanly tactilely discernible surface feature (340) indicating the rotational relationship between the hub (300) and the needle (100).

Figure 1:
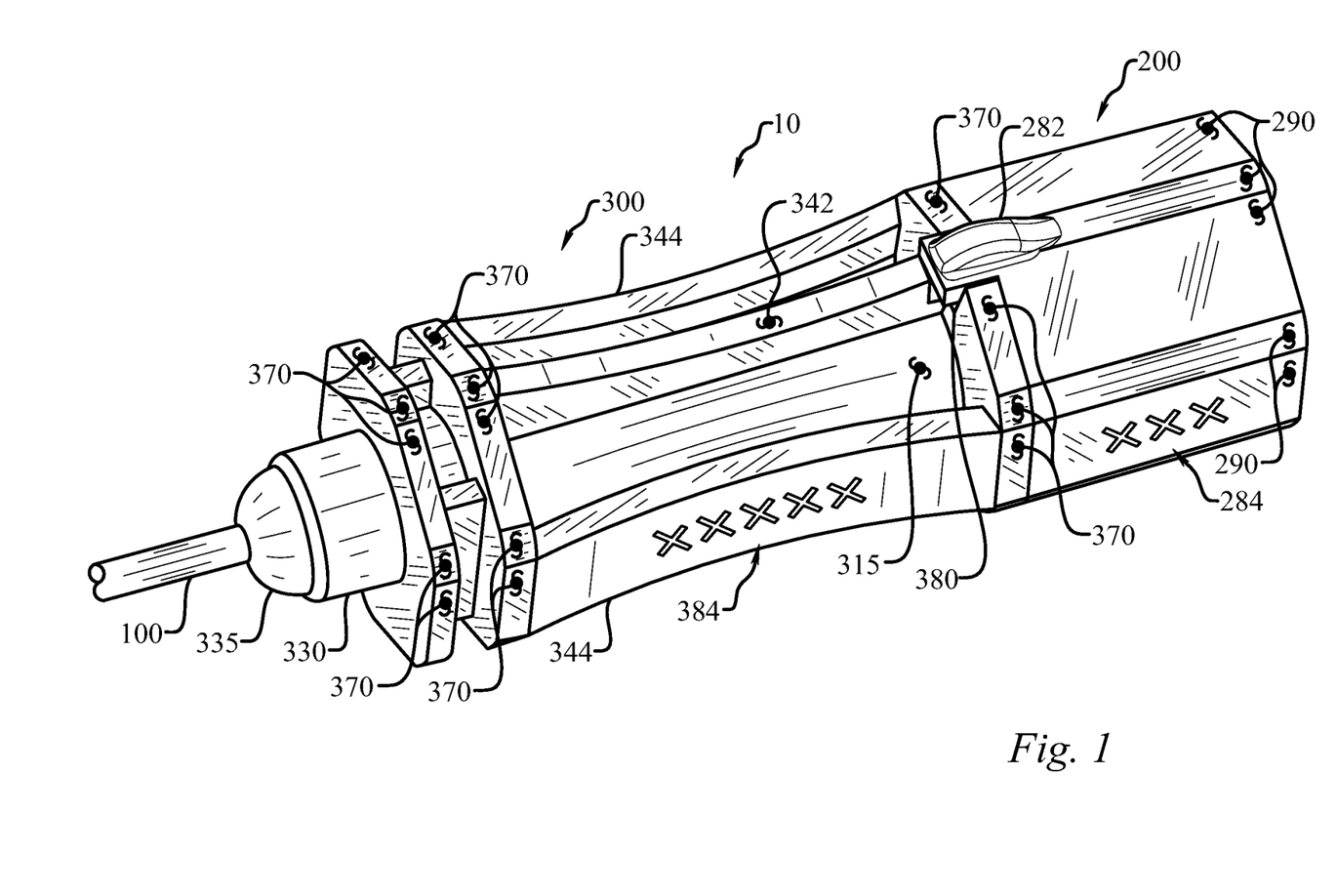
FIG. 1 is an elevated perspective view of a portion of an embodiment of the instant invention.
Figure 2:
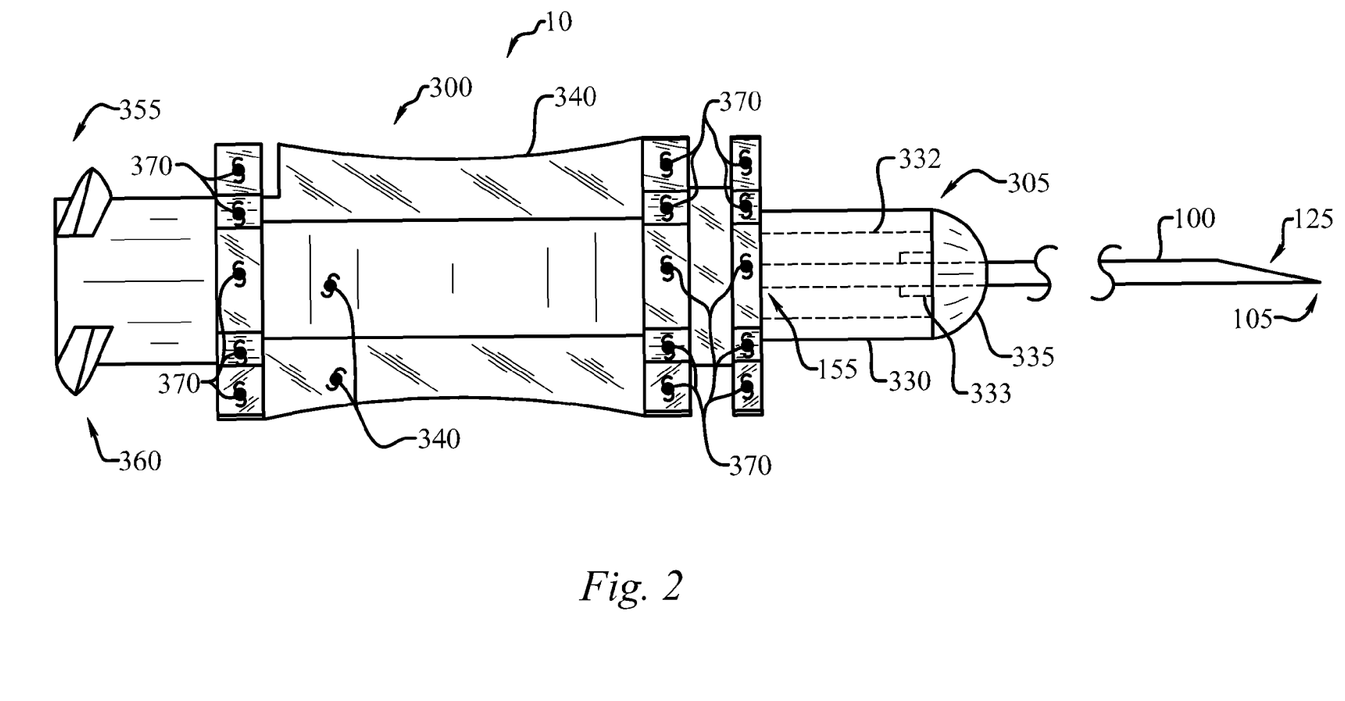
FIG. 2 is a side view of a portion of the embodiment of FIG. 1.
Figure 9:
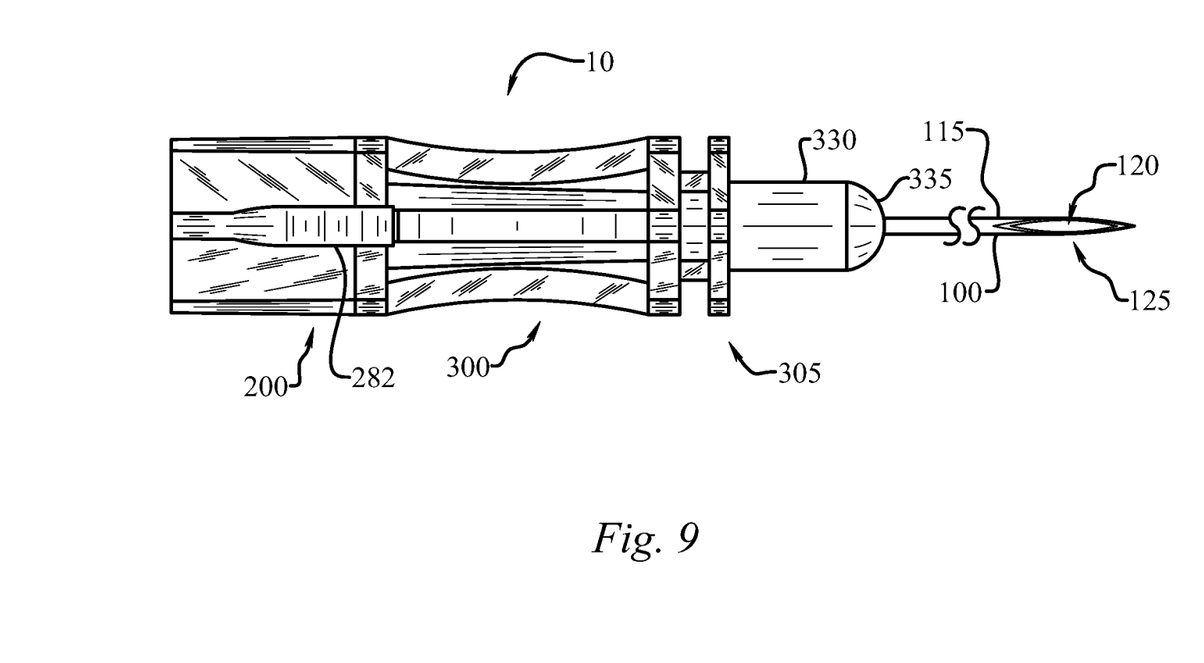
FIG. 9 is a top view of a portion of the embodiment of FIG. 1.

Thus, by touch alone, an operator grasping the hub (300) is immediately able to tell, by finger touch alone, the orientation of the needle port (120), and in those embodiments having a needle bevel (125) where the needle port is formed at least partially within the needle bevel (125), the directionality of the needle bevel (125) can likewise be ascertained, as seen well in FIGS. 1, 2, and 9.

Cooperating with the needle (100), the stylet proximal end (205) may formed with a stylet bevel (225), seen well in FIG. 3, cooperating with the needle bevel (125) in an insertion position to form a substantially uniform needle sidewall (115), as seen well in FIG. 9.

Figure 5:
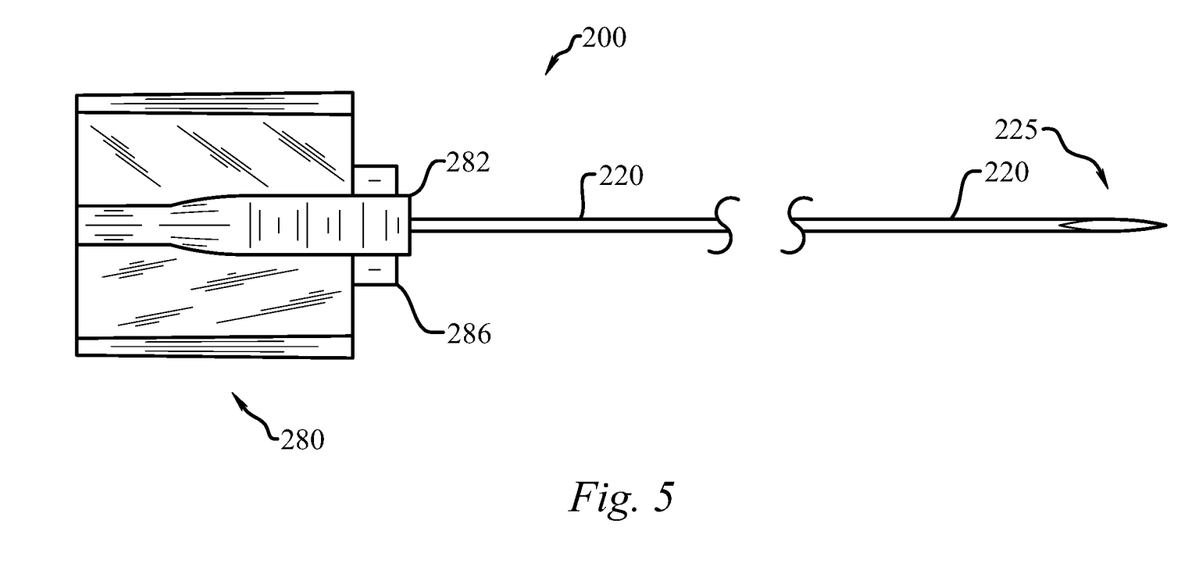
FIG. 5 is a top view of a portion of the embodiment of FIG. 1.

In other embodiments, as also seen well in FIG. 5, the stylet base (280) may be formed with a bevel index tab (282) in a predetermined rotational relationship with the stylet bevel (225) indicating said predetermined rotational relationship. Thus, the stylet (200) may effectively be locked into position when fully inserted into the needle (100), and would not be able to rotate independently of the needle (100).

In various other embodiments, the assembly (10) can include a stylet base (280) that also includes a hub occluder (286) which, as seen by way of example, in FIGS. 5 and 6, when in an insertion position, occludes at least a portion of the hub lumen (310). The hub-needle attachment (330) may be further formed with a needle sleeve (332) surrounding at least a portion of the needle distal end (155) and the needle sleeve (332) may substantially surround at least a portion of the hub lumen (310), as seen well in FIG. 6.

Figure 12:
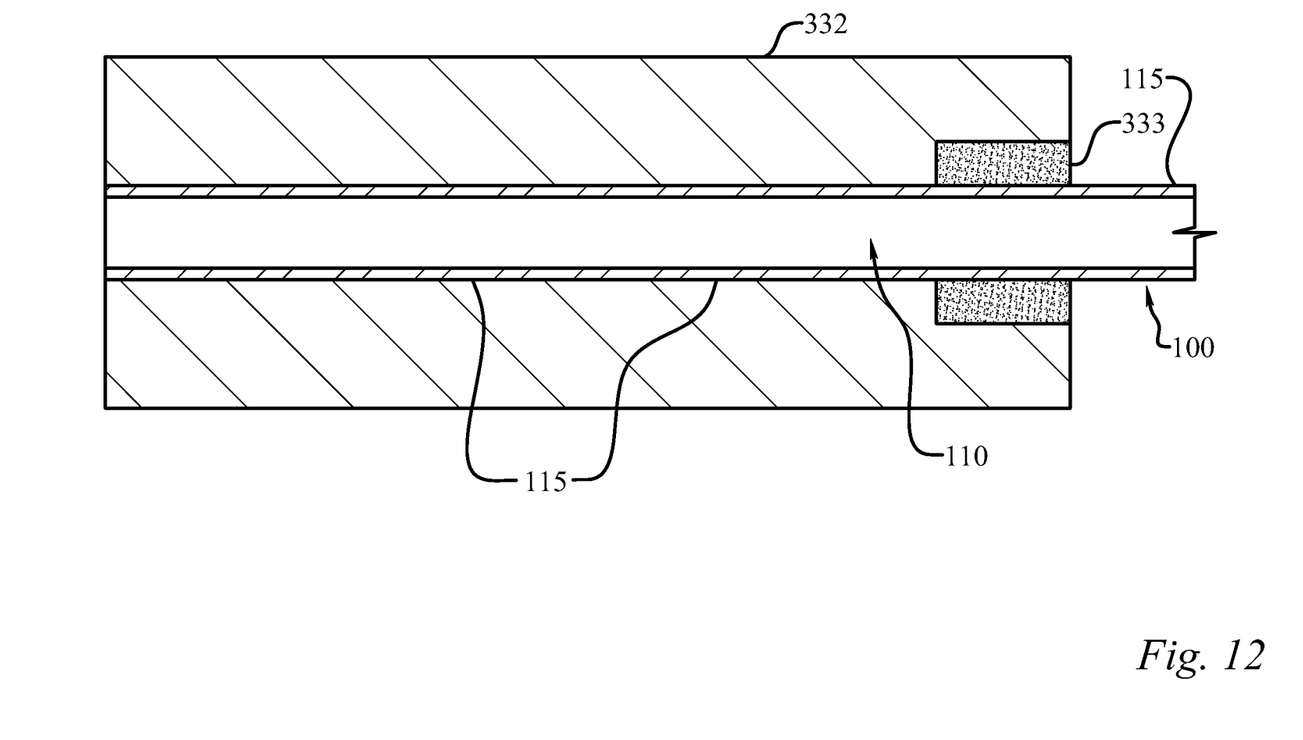
FIG. 12 is a section view taken along line 12-12 of FIG. 11.
Figure 13:
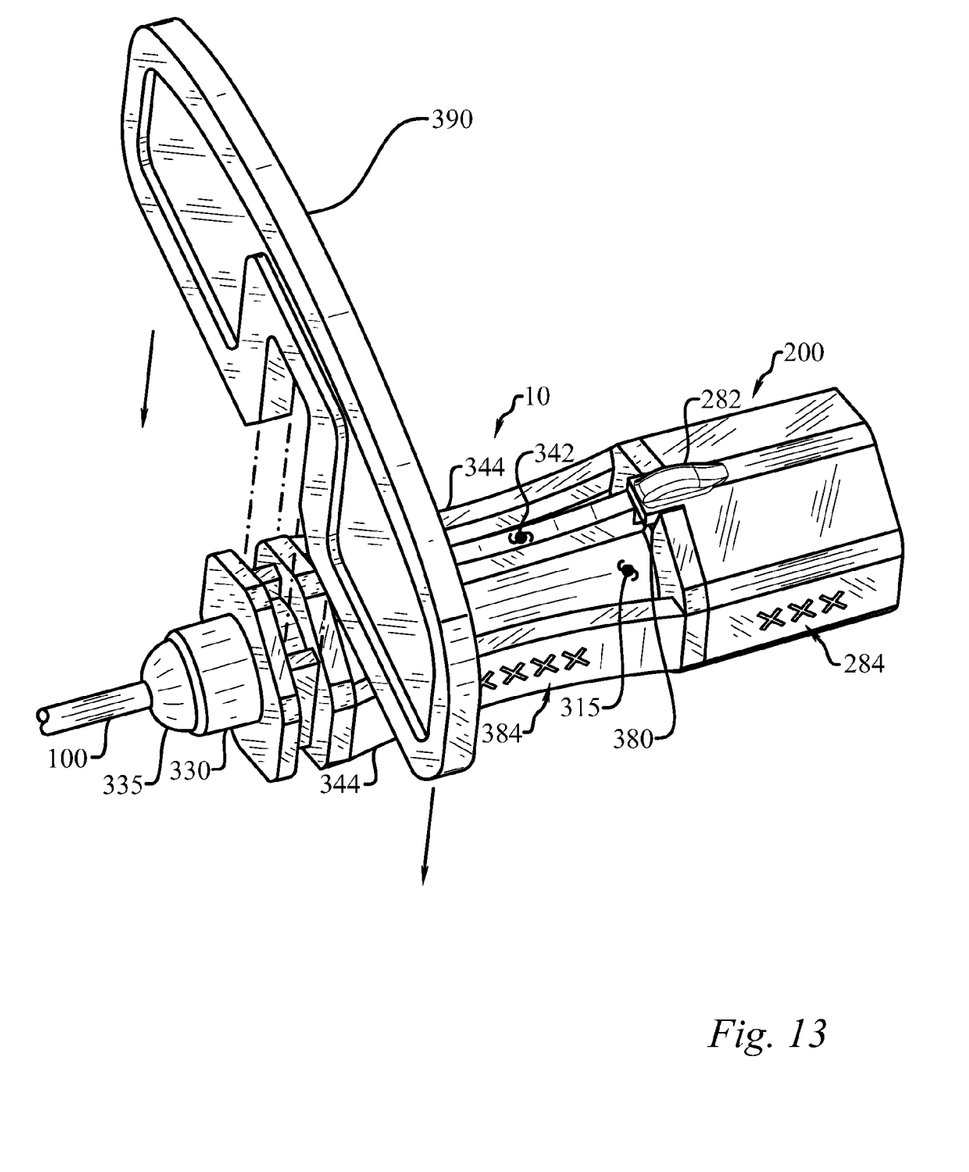
FIG. 13 is an elevated perspective view of an embodiment of the instant invention, showing a detachable wing hub.

With reference to FIG. 12, the needle sleeve (332) may be adhered at least a portion of the needle distal end (155) with needle sleeve bedding (333) and in another embodiment, at least a portion of the hub-needle attachment (330) may include attachment compound (335), seen well in FIG. 13. Any portion of any of the above detailed assembly (10) components may bear indicia (284, 384), seen well in FIG. 1, and/or may be color-coded, to represent such things as the size (gauge) of the needle, or needle type. Such visually perceptible indicia serves as an additional guide to the humanly tactilely discernible feature (340) and may be of any type perceptible to human vision. These would include colored components comprising all or part of the needle (100), stylet (200), and/or hub (300); as well as visually perceptible indicia of any kind on any portion of the assembly (10). In one particular embodiment at least a portion of the hub-needle attachment (330) comprises a same color indexed stylet base (280), needle sleeve (332) and attachment compound (335) to allow rapid visual identification and/or confirmation of assembly parameters, including but not limited to size (gauge) of the needle and needle type. It is particularly noted that color indexing does not require that each of the named elements be entirely colored, as it is envisioned that color bands, dots, or other color schemes may be sufficient to allow indexing of the elements.

As described in part above, many variations are possible in forming the humanly tactilely discernible feature (340). All or part of the feature may be an external surface bevel face orientation feature (342) indicating the direction of the needle bevel (125), seen well in FIGS. 1 and 4. Additionally, all or part of the feature (340) may include a bevel orthogonal orientation feature (344) indicating a position orthogonal, or at least a direction other than, to the direction of the needle bevel (125), also seen well in FIGS. 1 and 4. One skilled in the art will realize that there is essentially no limitation upon the nature of the humanly tactile discernible feature (340), other than it be recognizable to the operator and be in a predetermined fixed rotational position to any needle port (120) or needle bevel (125). Furthermore, the spatial relationship between features (340) may be of any type, and the orthogonal arrangement described above is only one of many possible embodiment relationships.

In various embodiments, the hub (300) further may further include a hub-externality connector (360), seen well in FIG. 10. By way of example and not limitation only, this could include a threaded portion suitable for attaching to some external device, again by way of limitation only, such as the well-known "Luer lock connector," that may be used to connect the assembly to a syringe, tubing, or the like, by means such as a thread (360).

Figure 7:
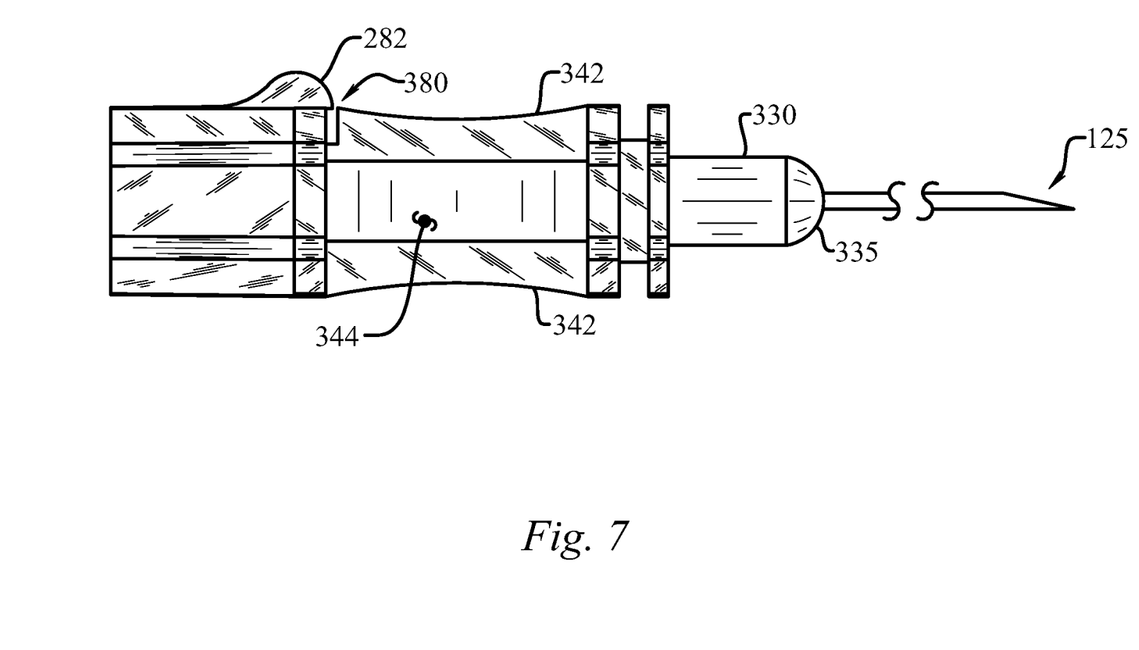
FIG. 7 is a side view of a portion of the embodiment of FIG. 1.
Figure 8:
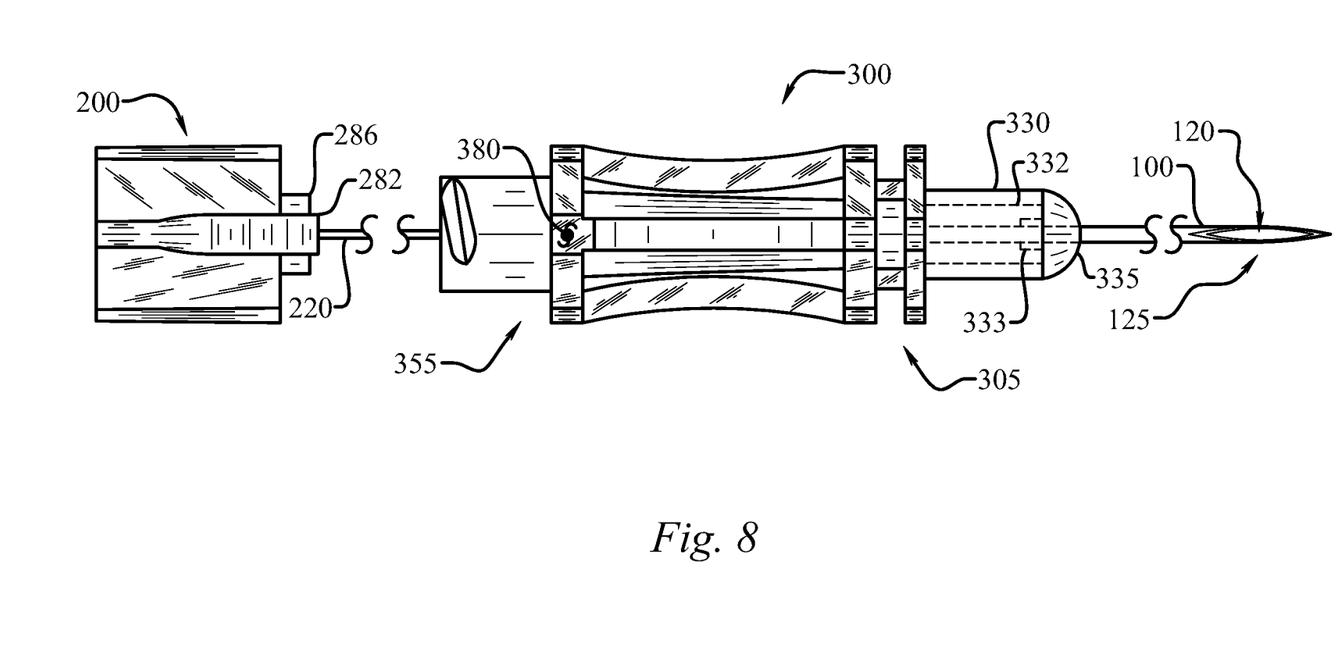
FIG. 8 is a partially exploded top view of a portion of the embodiment of FIG. 1.
Figure 14:
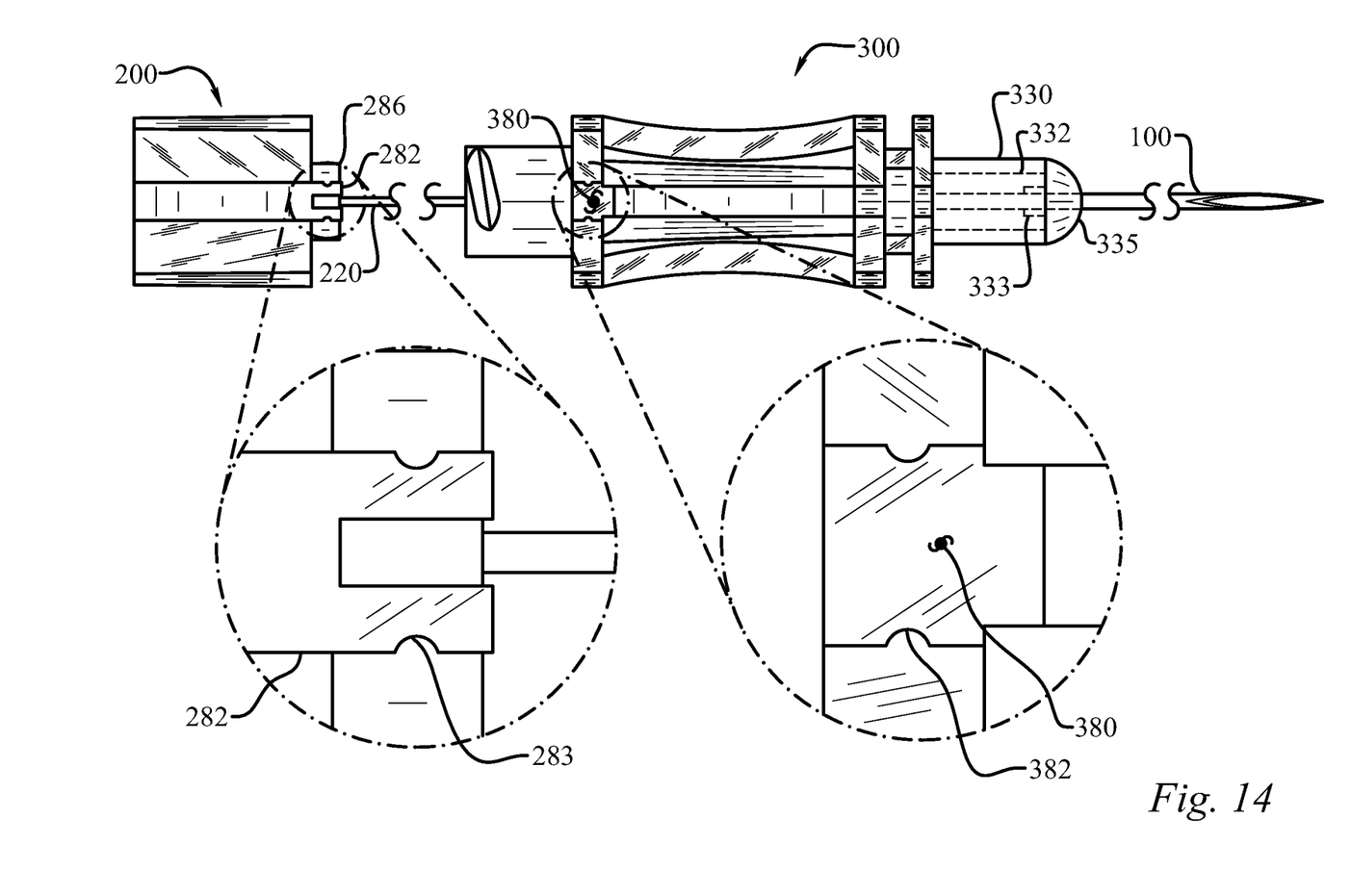
FIG. 14 is a top plan view of an embodiment of the instant invention, partially disassembled, showing details of the stylet and hub.
Figure 15:
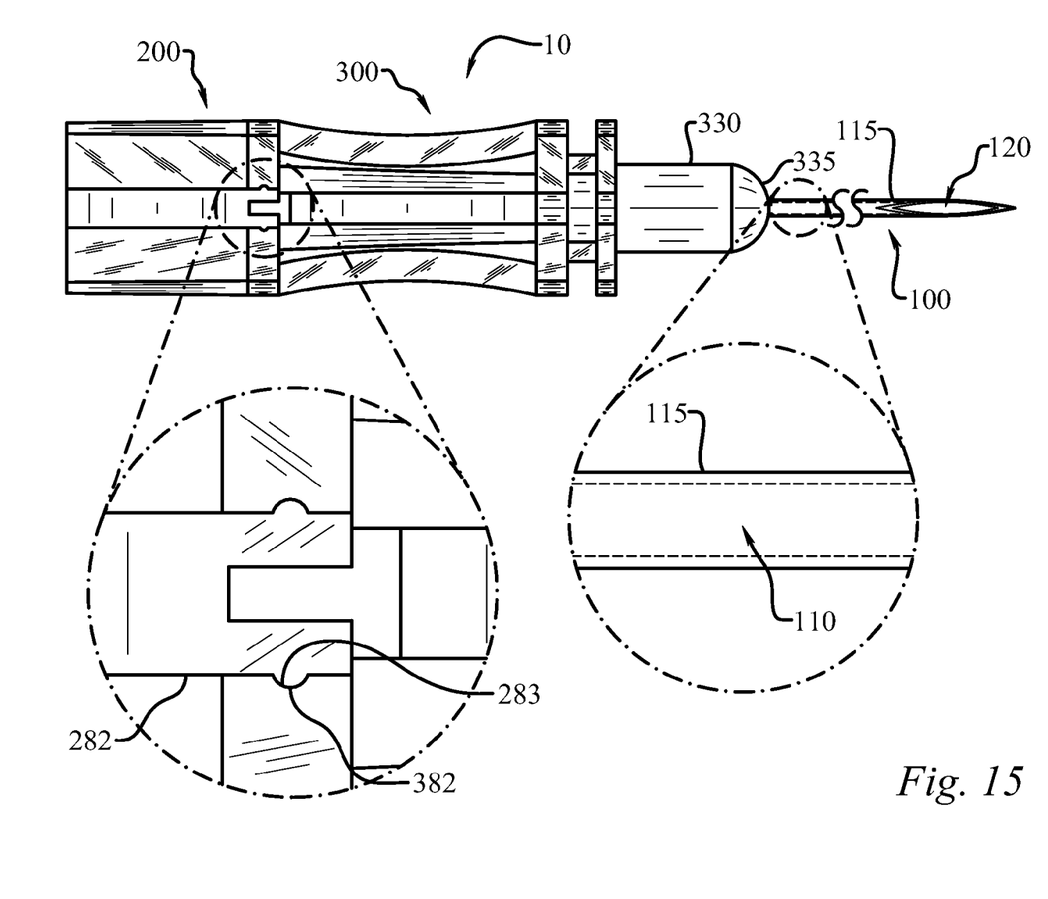
FIG. 15 is a top plan view of an embodiment of the instant invention, assembled, showing details of the stylet and hub.

In some embodiments, the bevel index tab (282) cooperates with a bevel index notch (380), seen well in FIGS. 3, 4, and 7, to indicate a predetermined rotational relationship between the needle (100), stylet (200) and hub (300), as seen well in FIGS. 7 and 9. Thusly engaged, and operating in cooperation with the humanly tactile discernible feature (340), the operator may be assured by touch alone, as to the rotational orientation of the entire assembly (10). Such easy tactile discrimination may be aided in other embodiments by the provision of stylet facets (290) that cooperate with a plurality of hub facets (370) indicating a predetermined rotational position between the stylet (200) and the hub (300), as seen in one embodiment in FIG. 1. Thus, the stylet base (280) and hub facets (370) may present a uniform tactile surface to aid in showing proper operational joining. To assist the stylet base (280) in maintaining a firm connection with the bevel index notch (380), the bevel index tab (282) may be configured as a split-tab to create resilience tending to hold pressure against the walls of the bevel index notch (380), as seen in FIGS. 14 and 15. In other embodiments, also seen in FIGS. 14 and 15, a stylet hub retainer (283) may be configured so as to cooperate with a hub-stylet retainer (382) to provide an additional reversible locking action between the stylet (200) and the hub (300). The retainers (283, 382) may be designed in any mutually cooperative manner so as to help secure the stylet (200) and hub (300).

Because of the relatively small size of the assembly (10) in many embodiments, the hub (300) may be provided with a hub wing (390) to make gripping easier, as seen in an exemplary embodiment in FIG. 13. As would be seen by one skilled in the art, the hub wing (390) may be releasable or nonreleasable, may be of any convenient shape or size, and may bear any type of visually or tactilely discernible features found useful to users.

In an exemplary embodiment, such as those seen well in FIGS. 1, 9, 10, and 13; but one that is not intended as a limitation of any kind, the needle hub (300) may be configured with two external surface bevel face orientation features (342) in the form of narrow ribs, one rotationally aligned with the needle bevel (125) and one a hundred and eighty degrees radially displaced from the needle bevel (125). In the case where there may be more than one external surface bevel face orientation feature (342), it may be desirable that these features have tactilely separable characteristics.

In some embodiments, the bevel face orientation feature (342) may include a first bevel orientation feature (342) having a first discernible tactile configuration, and a second bevel orientation feature (342) having a second discernible tactile configuration. In such an embodiment, it would be possible to have the first bevel orientation feature (342) identifying a lumen side of the needle bevel (125) and the second bevel orientation feature (342) identifying a side of the needle (100) directly opposite the lumen side of the needle bevel (125). In other embodiments, different tactile configurations of any of the humanly tactilely discernible surface features (340) may identify any particular aspect of the rotational position of a needle (100) as may be desired by a designer.

In some embodiments, there may be two other bevel orthogonal orientation features (344) in the form of wide ribs, one ninety degrees radially displaced from the needle bevel (125) and one two hundred and seventy degrees radially displaced from the needle bevel (125). An operator pinching the hub between a thumb and forefinger thus immediately feels these orientation features (342, 344). When the assembly (10) and thereby the needle bevel (125), is rotated between the thumb and forefinger, these differing orientation features (342, 344) rotate as well, and the difference in tactile sensation immediately alerts the operator to the position of the needle bevel (125).

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative manufacturing processes and materials, relative arrangement of elements, and dimensional configurations. Accordingly, even though only few variations of the present invention are described herein, it is to be understood that the practice of such additional modifications and variations and the equivalents thereof, are within the spirit and scope of the invention as defined in the following claims. The corresponding structures, materials, acts, and equivalents of all means or step plus function elements in the claims below are intended to include any structure, material, or acts for performing the functions in combination with other claimed elements as specifically claimed.

I claim:

1. A rotational orientation indicating hollow needle assembly (10), comprising;
   a needle (100) having a needle lumen (110) surrounded at least in part by a needle sidewall (115) connecting a needle proximal end (105) formed with a needle bevel (125), a needle distal end (155), and a needle port (120) at least partially within the needle bevel (125);
   a stylet (200), substantially reversibly occluding the needle lumen (110) in an insertion position, having a stylet shaft (220) with a stylet proximal end (205), a stylet distal end (275), and a stylet base (280); and
   a hub (300) having a hub lumen (310) surrounded at least in part by a hub sidewall (315), connecting a hub proximal end (305) and a hub distal end (355), wherein the hub proximal end (305) is attached in a predetermined rotational relationship to the needle distal end (155) at a hub-needle attachment (330), thereby placing the hub lumen (310) in fluid communication with the needle lumen (110), and the hub sidewall (315) has at least one external surface formed with at least one humanly tactilely discernible surface feature (340) further comprising an external surface bevel face orientation feature (342) indicating the direction of the needle bevel (125) and wherein the bevel face orientation feature (342) further comprises a first bevel orientation feature (342) having a first discernible tactile configuration, and a second bevel orientation feature (342) having a second discernible tactile configuration, and wherein the first bevel orientation feature (342) identifies a lumen side of the needle bevel (125) and the second bevel orientation feature (342) identifies a side of the needle (100) directly opposite the lumen side of the needle bevel (125), indicating the rotational relationship between the hub (300) and the needle (100).

2. The needle assembly according to claim 1, wherein the stylet proximal end (205) is formed with a stylet bevel (225) cooperating with the needle bevel (125) in an insertion position to form a substantially concentric uniform need sidewall (115).

3. The needle assembly according to claim 1, wherein the stylet base (280) is formed with a bevel index tab (282) in a predetermined rotational relationship with the stylet (220) indicating said predetermined rotational relationship.

4. The needle assembly according to claim 1, wherein the stylet base (280) further comprises a hub occluder (286) which, in an insertion position, occludes at least a portion of the hub lumen (310).

5. The needle assembly according to claim 1, wherein the hub-needle attachment (330) is further formed with a needle sleeve (332) surrounding at least a portion of the needle distal end (155) and the needle sleeve (332) is substantially surrounded by at least a portion of the hub lumen (310).

6. The needle assembly according to claim 5, wherein at least a portion of the hub-needle attachment (330) comprises at least a same color indexed as the stylet base (280) and the needle sleeve (332).

7. The needle assembly according to claim 1, wherein the hub needle attachment (330) further comprises a needle sleeve bedding (333).

8. The needle assembly according to claim 1, wherein at least a portion of the hub-needle attachment (330) comprises an attachment compound (335).

9. The needle assembly according to claim 8, wherein at least a portion of the hub-needle attachment (330) comprises at least a same color indexed as the stylet base (280) and the attachment compound (335).

10. The needle assembly according to claim 1, wherein the humanly tactilely discernible feature (340) is a bevel orthogonal orientation feature (344) indicating a position orthogonal to the direction of the needle bevel (125).

11. The needle assembly according to claim 1, wherein the hub (300) further comprises a hub-externality connector (360).

12. The needle assembly according to claim 1, wherein the stylet base (280) further comprises a bevel index tab (282) cooperating with a bevel index notch (380) to indicate a predetermined rotational relationship between the needle (100), stylet (200) and hub (300).

13. The needle assembly according to claim 1, wherein a plurality of stylet facets (290) cooperate with a plurality of hub facets (370) indicating a predetermined rotational position between the stylet (200) and the hub (300).

14. The needle assembly according to claim 1, wherein the hub (300) further comprises a releasable hub wing (390).

15. The needle assembly according to claim 1, wherein stylet base (280) further comprises a stylet-hub retainer (283) reversibly cooperating with a hub-stylet retainer (382) on the bevel index notch (380) to form a reversible mechanical connection between the stylet (200) and the hub (300).

16. A rotational orientation indicating hollow needle assembly (10), comprising;
- a needle (100) having a needle lumen (110) surrounded at least in part by a needle sidewall (115) connecting a needle proximal end (105) formed with a needle bevel (125), a needle distal end (155), and a needle port (120) formed at least partially within the needle bevel (125);
- a stylet (200), substantially reversibly occluding the needle lumen (110) in an insertion position, having a stylet shaft (220) with a stylet proximal end (205), a stylet distal end (275), and a stylet base (280); and
- a hub (300) having a hub lumen (310) surrounded at least in part by a hub sidewall (315), connecting a hub proximal end (305) and a hub distal end (355), wherein the hub proximal end (305) is attached in a predetermined rotational relationship to the needle distal end (155) at a hub-needle attachment (330), thereby placing the hub lumen (310) in fluid communication with the needle lumen (110), and the hub sidewall (315) has at least one external surface bevel face orientation feature (342) indicating the direction of the needle bevel (125) and at least one bevel orthogonal orientation feature (344) indicating a position orthogonal to the direction of the needle bevel (125).

17. A rotational orientation indicating hollow needle assembly (10), comprising;
- a needle (100) having a needle lumen (110) surrounded at least in part by a needle sidewall (115) connecting a needle proximal end (105) formed with a needle bevel (125), a needle distal end (155), and a needle port (120) at least partially within the needle bevel (125);
- a stylet (200), substantially reversibly occluding the needle lumen (110) in an insertion position, having a stylet shaft (220) with a stylet proximal end (205), a stylet distal end (275), and a stylet base (280); and
- a hub (300) having a hub lumen (310) surrounded at least in part by a hub sidewall (315), connecting a hub proximal end (305) and a hub distal end (355), wherein the hub proximal end (305) is attached in a predetermined rotational relationship to the needle distal end (155) at a hub-needle attachment (330), thereby placing the hub lumen (310) in fluid communication with the needle lumen (110), and the hub sidewall (315) has at least one external surface formed with at least one humanly tactilely discernible surface feature (340) further comprising a bevel orthogonal orientation feature (344) indicating a position orthogonal to the direction of the needle bevel (125) thereby indicating the rotational relationship between the hub (300) and the needle (100).

18. The needle assembly according to claim 17, wherein the hub-needle attachment (330) is further formed with a needle sleeve (332) surrounding at least a portion of the needle distal end (155) and the needle sleeve (332) is substantially surrounded by at least a portion of the hub lumen (310).

19. The needle assembly according to claim 18, wherein at least a portion of the hub-needle attachment (330) comprises at least a same color indexed as the stylet base (280) and the needle sleeve (332).

* * * * *